United States Patent
Doi et al.

(10) Patent No.: US 8,885,250 B2
(45) Date of Patent: Nov. 11, 2014

(54) SURGICAL MICROSCOPE SYSTEM

(75) Inventors: Masao Doi, Fuchu (JP); Toshio Yamazaki, Mitaka (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 298 days.

(21) Appl. No.: 13/059,351

(22) PCT Filed: Aug. 18, 2009

(86) PCT No.: PCT/JP2009/064419
§ 371 (c)(1),
(2), (4) Date: Feb. 16, 2011

(87) PCT Pub. No.: WO2010/021319
PCT Pub. Date: Feb. 25, 2010

(65) Prior Publication Data
US 2011/0134518 A1  Jun. 9, 2011

(30) Foreign Application Priority Data
Aug. 19, 2008  (JP) .................. 2008-210516

(51) Int. Cl.
*G02B 21/00*   (2006.01)
*A61B 19/00*   (2006.01)

(52) U.S. Cl.
CPC .................. *A61B 19/5223* (2013.01)
USPC ....................................... 359/384

(58) Field of Classification Search
None
See application file for complete search history.

(56) References Cited

U.S. PATENT DOCUMENTS

| | | | |
|---|---|---|---|
| 5,528,417 A | | 6/1996 | Nakamura |
| 5,552,929 A | * | 9/1996 | Fukaya et al. ................ 359/380 |
| 6,473,229 B2 | * | 10/2002 | Nakamura ..................... 359/377 |
| 2004/0095639 A1 | | 5/2004 | Mora |
| 2008/0123184 A1 | * | 5/2008 | Hege et al. .................... 359/383 |
| 2008/0231948 A1 | | 9/2008 | Nakamura et al. |
| 2009/0190209 A1 | | 7/2009 | Nakamura |

FOREIGN PATENT DOCUMENTS

| | | |
|---|---|---|
| EP | 0 628 290 AI | 12/1994 |
| EP | 1 420 280 A1 | 5/2004 |
| JP | 2825721 B2 | 9/1998 |
| JP | 11-231226 A | 8/1999 |
| JP | 2004-167240 A | 6/2004 |
| WO | 94/14387 | 7/1994 |

OTHER PUBLICATIONS

U.S. Appl. No. 12/946,148 to Masao Doi et al., which was filed on Nov. 15, 2010.

* cited by examiner

*Primary Examiner* — Derek S Chapel
(74) *Attorney, Agent, or Firm* — Greenblum & Bernstein, P.L.C.

(57) ABSTRACT

Only a front end part 16 of a surgical microscope 15 is turned in a left-right direction X around a main axis S, so that an observation angle of a surgical site T is freely changed in the left-right direction. Even if the observation angle is changed, the orientation of eyepieces 22 is unchanged, and therefore, an operator does not need to bend his or her neck and no burden is imposed on the neck of the operator even if the operator must conduct an operation that takes a long time.

6 Claims, 7 Drawing Sheets

SURGICAL MICROSCOPE SYSTEM

TECHNICAL FIELD

The present invention relates to a surgical microscope system, and particularly, to a surgical microscope system capable of changing an observation direction without changing the position of an eyepiece unit.

BACKGROUND TECHNOLOGY

A surgical microscope used for, for example, neurosurgery is supported with a suspension arm at a front end of a support arm of a stand apparatus and is used in this state. To freely change an observation direction, the surgical microscope is supported with the suspension arm so that the surgical microscope is freely movable in front-rear and left-right directions.

More precisely, as disclosed in Japanese Patent Publication No. 2825721, the suspension arm itself consists of a small parallel linkage so that the suspension arm itself deforms to turn (incline) the surgical microscope supported at a lower end of the suspension arm in the left-right direction. The surgical microscope is supported at the lower end of the suspension arm with a shaft so that the surgical microscope freely turns in the front-rear direction around a horizontal rotation axis. Accordingly, in terms of the viewing direction of an observer, the surgical microscope freely turns in the left-right and front-rear directions to optionally change an observation direction.

DISCLOSURE OF INVENTION

According to the related art, however, the surgical microscope is configured to entirely turn in the left-right and front-rear directions. When an observation angle is changed in, in particular, the left-right direction, the operator must turn his or her neck. This puts a heavy burden on the neck if the operation takes a long time.

Means to Solve the Problems

In consideration of the problems of the related art, the present invention provides a surgical microscope system capable of changing an observation angle in a left-right direction without requiring an operator to turn his or her neck.

A technical aspect of the present invention provides a surgical microscope system having a suspension arm downwardly extending from a front end of a horizontally extending support arm of a stand apparatus, a lower end of the suspension arm supporting a surgical microscope so that the surgical microscope freely turns in front-rear and left-right directions. The surgical microscope substantially has a cylindrical structure provided with a pair of eyepieces and a light flux intake. In the surgical microscope, a front end part including the light flux intake is so supported as to freely and independently turn in the left-right direction around a main axis passing through a sectional center of the surgical microscope. A main body of the surgical microscope excluding the front end part is so supported with a shaft as to freely turn in the front-rear direction relative to the lower end of the suspension arm around a horizontal axis orthogonal to the main axis.

MODE OF IMPLEMENTING INVENTION

First Embodiment

FIGS. 1 to 6 are views illustrating the first embodiment of the present invention. In the explanations mentioned above and below, the left-right direction is a left-right direction with respect to the observing direction of an operator and the front direction is the observing direction of the operator.

Stand Apparatus

Figure 1:
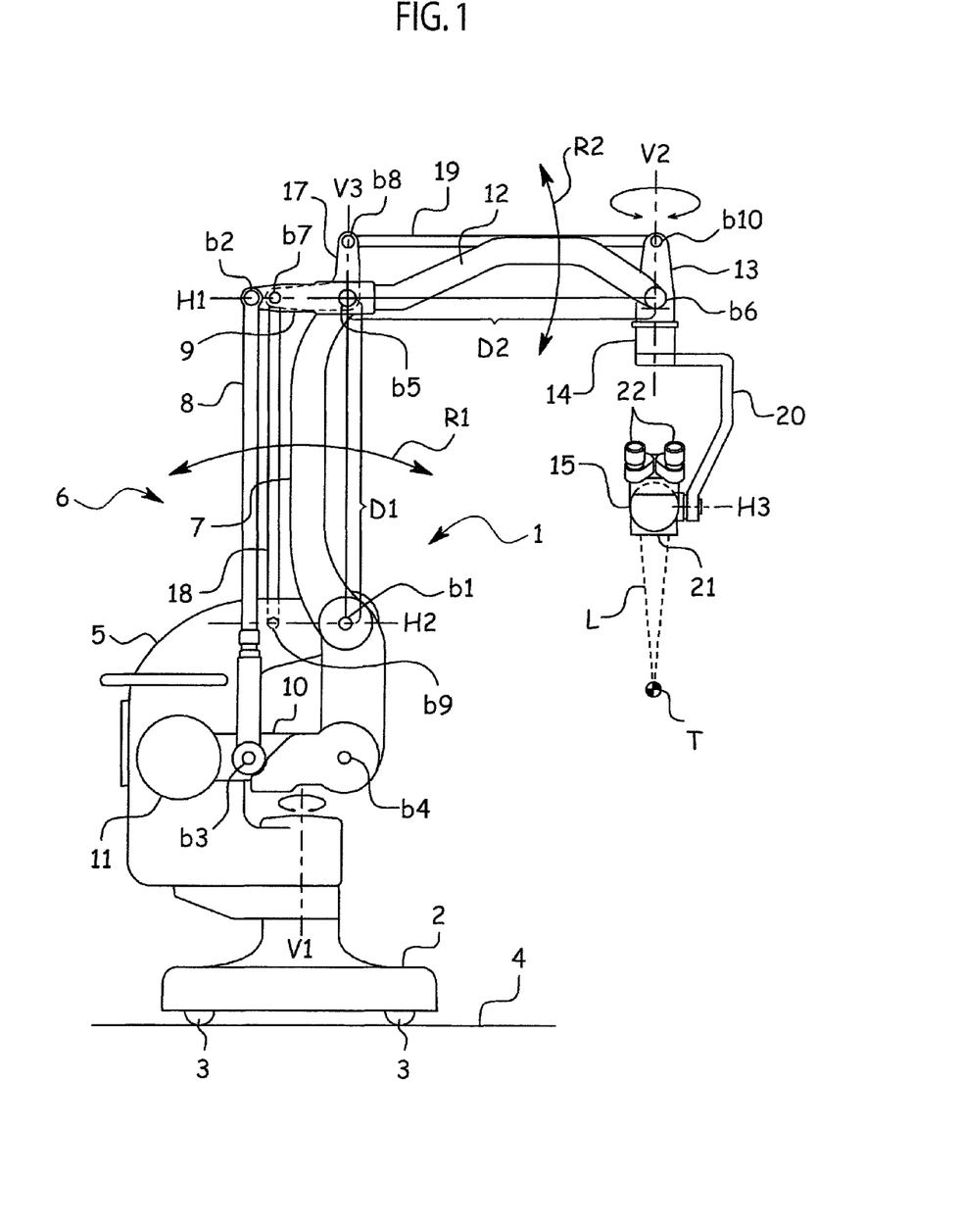
FIG. 1 is a side view illustrating a surgical microscope system according to a first embodiment of the present invention.

A stand apparatus 1 will be explained. A numeral 2 represents a base and a bottom surface of the base 2 has casters 3 provided with a lock mechanism. With the casters 3, the stand apparatus 1 is movable on a floor 4. On an upper part of the base 2, there is a main body 5 having a C-shaped side face. The main body 5 is freely rotatable around a vertical shaft V1. The vertical shaft V1 has an electromagnetic clutch to lock and free the rotation of the main body 5.

A rotation axis point b1 at an upper part of the main body 5 supports with a shaft a parallel linkage 6. The parallel linkage 6 has two parallel longitudinal links 7 and 8 and two parallel lateral links 9 and 10 that are connected together at connection axis points b2 to b5. A lower midpoint of the longitudinal link 7 of the parallel linkage 6 is supported with the shaft at the rotation axis point b1. The rotation axis point b1 is provided with an electromagnetic clutch to lock and free the rotation of the longitudinal link 7 in a lateral direction R1.

The longitudinal link 7 supported with the shaft at the rotation axis point b1 is a side of a parallelogram defined with the rotation axis points b2 to b5 and is inwardly curved to secure a work space and avoid an interference with a main operator. The lower lateral link 10 is provided with a counterweight 11.

The upper lateral link 9 of the parallel linkage 6 is horizontally extended to integrally form a support arm 12. A front end of the support arm 12 is provided with a vertical front link 13 that is freely rotatable around a connection axis point b6. The support arm 12 is upwardly curved to secure a work space and avoid an interference with the head of the main operator.

A lower part of the front link 13 is a support box 14 that is horizontally rotatable around a vertical axis V2.

A start point of the support arm 12, i.e., the connection axis point b5 supports through a shaft an L-shaped crank member 17. The crank member 17 has a horizontal axis point b7 that is positioned at a horizontal level H1 on which the connection axis point b5 is present and a vertical axis point b8 that is positioned on a vertical line V3 on which the connection axis point b5 is present.

The horizontal axis point b7 and a connection axis point b9 of the main body 5 that is positioned on a horizontal level H2 at which the rotation axis point b1 is present are connected to each other with a longitudinal sub-link 18 that is in parallel with the longitudinal link 7 and has the same length as a virtual straight line D1. The longitudinal link 7 is defines the straight line D1 between the rotation axis point b1 and the connection axis point b5. Accordingly, a parallel sub-linkage defined with the rotation axis point b1 and connection axis points b9, b7, and b5 always maintains a link b5-b7 to be in parallel with a link b9-b1 positionally fixed to the main body 5.

The vertical axis point b8 of the crank member 17 is connected to an upper connection axis point b10 of the front link 13 with a lateral sub-link 19 that is in parallel with the support arm 12 and has the same length as a virtual straight line D2. The support arm 12 defines the straight line D2 between the connection axis points b5 and b6. Accordingly, a parallel sub-linkage defined with the connection axis points b5, b8, b10, and b6 always maintains a link b10-b6 to be in parallel with a link b5-b8. The parallel sub-linkage defined by the rotation axis point b1 and connection axis points b9, b7, and b5 is fixed to the main body 5 on one side thereof and is connected through the crank member 17 to the parallel sub-linkage defined by the connection axis points b5, b8, b10, and b6. As results, the front link 13, i.e., one side of the latter parallel sub-linkage and the rotation axis V2 always keep a fixed angle with respect to the link b9-b1.

In this way, the longitudinal sub-link 18, crank member 17, and lateral sub-link 19 always keep the front link 13 in a vertical position because the crank member 17 does not rotate even if the electromagnetic clutches of the stand apparatus 1 are freed to turn the parallel linkage 6 in the lateral position R1 around the rotation axis point b1, or the support arm 12 in a longitudinal position R2 around the connection axis point b5, or both at the same time.

Figure 2:
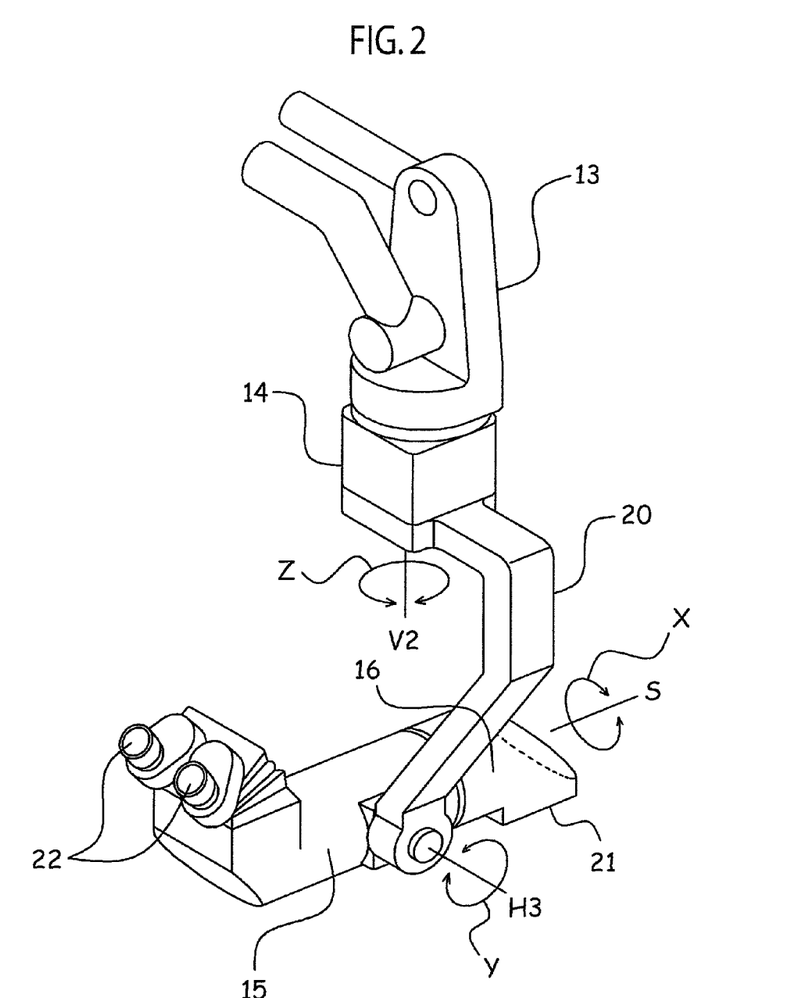
FIG. 2 is a perspective view illustrating a suspension arm and surgical microscope.

The support box 14 of the front link 13 that is maintained in a vertical position as mentioned above supports a surgical microscope 15 through a suspension arm 20 having an inverted L-shape. The suspension arm 20 is attached to a bottom face of the support box 14, and together with the support box 14, is rotatable in a horizontal direction Z around the vertical axis V2. The rotation around the vertical axis V2 is locked and freed with an electromagnetic clutch.

In this specification, each side element of the parallel linkage is typically a link rod. However, this does not limit the present invention. The parallel linkage according to the present invention may be made of two sprockets, a tensile endless chain or a part thereof serving as a force transmission element, and a link rod to support centers of the two sprockets and apply tensile force. In this case, ends of acting zones of the sprockets (or part thereof) and chain are parting/contacting points serving as joints to define the parallel linkage. Such a chain mechanism is applicable to the parallel sub-linkage connected to the crank member 17 of the present invention. In this case, one of the sprockets is fixed to or integrally formed with a connection element.

Surgical Microscope

Figure 3:
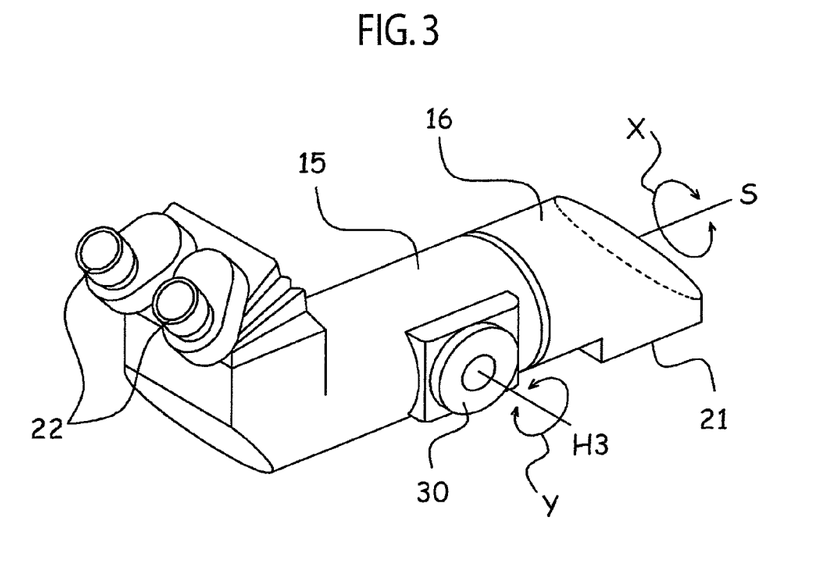
FIG. 3 is a perspective view illustrating the surgical microscope.
Figure 5:
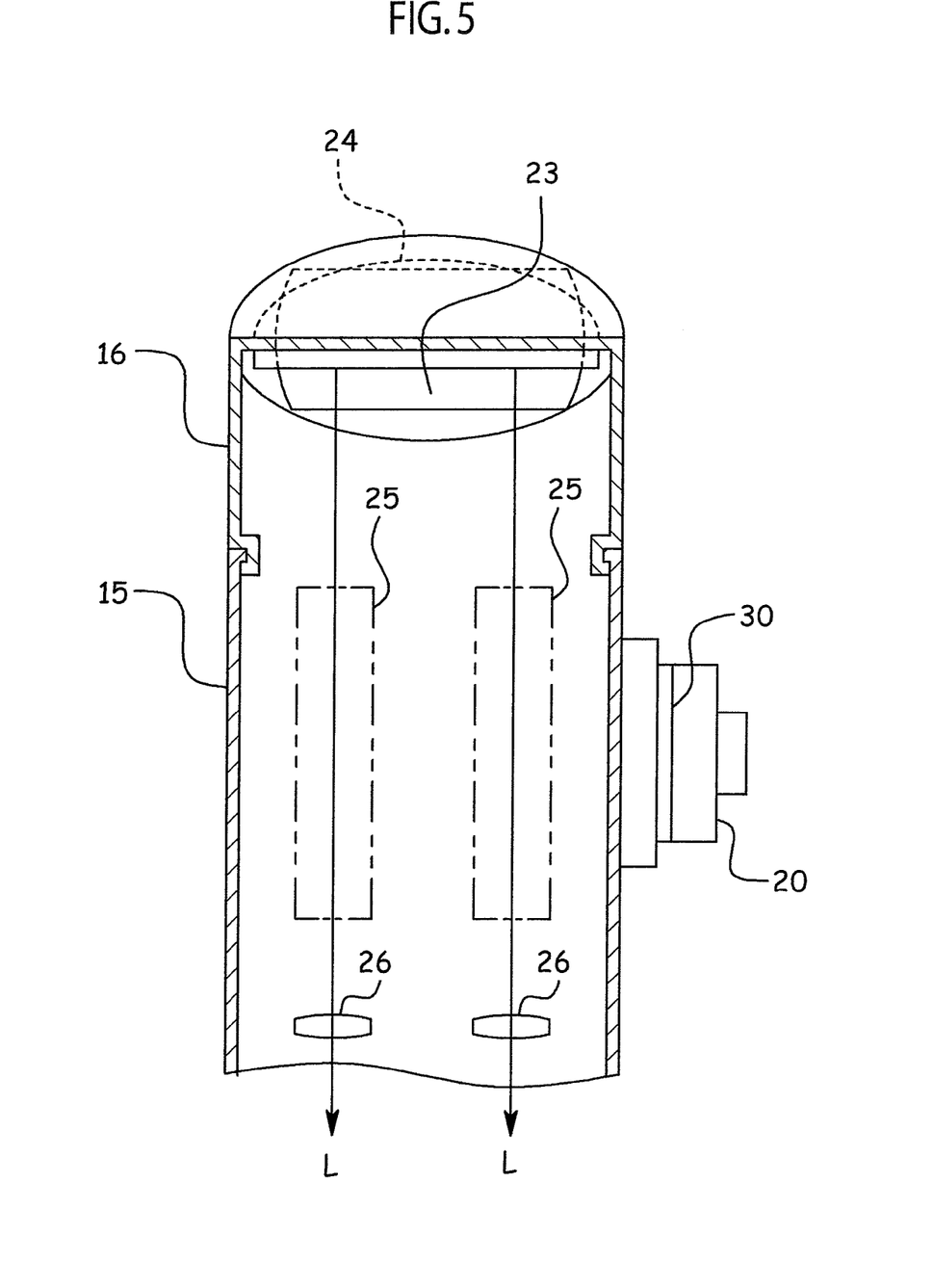
FIG. 5 is a sectional view of the surgical microscope.

The surgical microscope 15 extends horizontally and substantially has a cylindrical shape. On this side of the surgical microscope 15, it has a pair of eyepieces 22, and on a bottom surface thereof on the other side, it has a light flux intake 21 to take light flux L from a surgical site T. A front end part 16 including the light flux intake 21 is separated from a main body and is independently rotatable in a left-right direction X around a main axis S passing through a sectional center of the surgical microscope 15. Between the main body of the surgical microscope 15 and the front end part 16, predetermined frictional force is applied to maintain the front end part 16 at a rotated position. Instead of the frictional force, an electromagnetic clutch is employable to lock and free the front end part 16.

Figure 4:
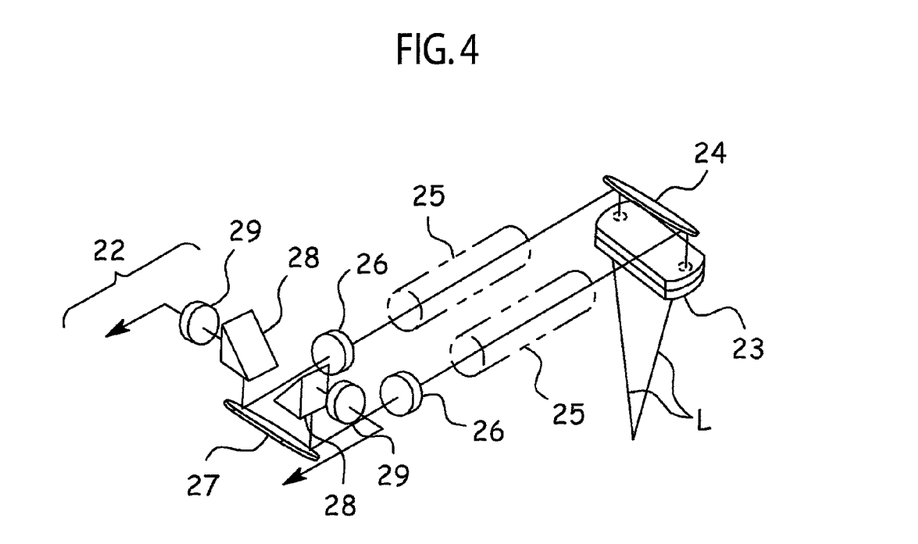
FIG. 4 is a perspective view illustrating an optical structure in the surgical microscope.

The light flux L entering the light flux intake 21 of the front end part 16 is passed through an object lens 23, is horizontally reflected by a first mirror 24, is passed through zoom lenses 25, reaches imaging lenses 26, is reflected by a second mirror 27, is passed through prisms 28 and lenses 29 of the eyepieces 22, and enters the eyes of the operator. The object lens 23 may horizontally be laid between the first mirror 24 and the zoom lenses 25 instead of vertically laying under the first mirror 24.

The main body of the surgical microscope 15 has an attaching face 30 to which a lower end of the suspension arm 20 is attached such that the surgical microscope 15 is rotatable in a front-rear direction Y around a horizontal axis H3. The main axis S is the sectional center of the cylindrical shape and is orthogonal to the horizontal axis H3 that is orthogonal to the vertical axis V2. A crossing point of the main axis S of the cylindrical shape and the horizontal axis H3 is on an extension of the vertical axis V2.

Accordingly, the horizontal axis H3 is always orthogonal to the front link 13 through the suspension arm 20. A virtual plane in which the horizontal axis H3 turns around the axis V2 is in parallel with the link b9-b1 fixed to the main body 5 and is horizontal.

The surgical microscope 15 is capable of turning in the front-rear direction Y around the horizontal axis H3. Predetermined frictional force is applied to the horizontal axis H3, to maintain the surgical microscope 15 at a position turned in the front-rear direction Y. Instead of the frictional force, an electromagnetic clutch is employable to lock and free the surgical microscope 15.

Rotation in the front-rear direction Y around the horizontal axis H3 only causes the eyepieces 22 to vertically move, and therefore, the operator does not need to bend his or her neck.

To change the observation direction in the left-right direction X, the operator holds only the front end part 16 of the surgical microscope 15 with his or her hand and turns the front end part 16 in the left-right direction X around the main axis S. According to an angular change, the first mirror 24 turns and takes the light flux L so that the light flux L is observed with the eyepieces 22.

Figure 6:
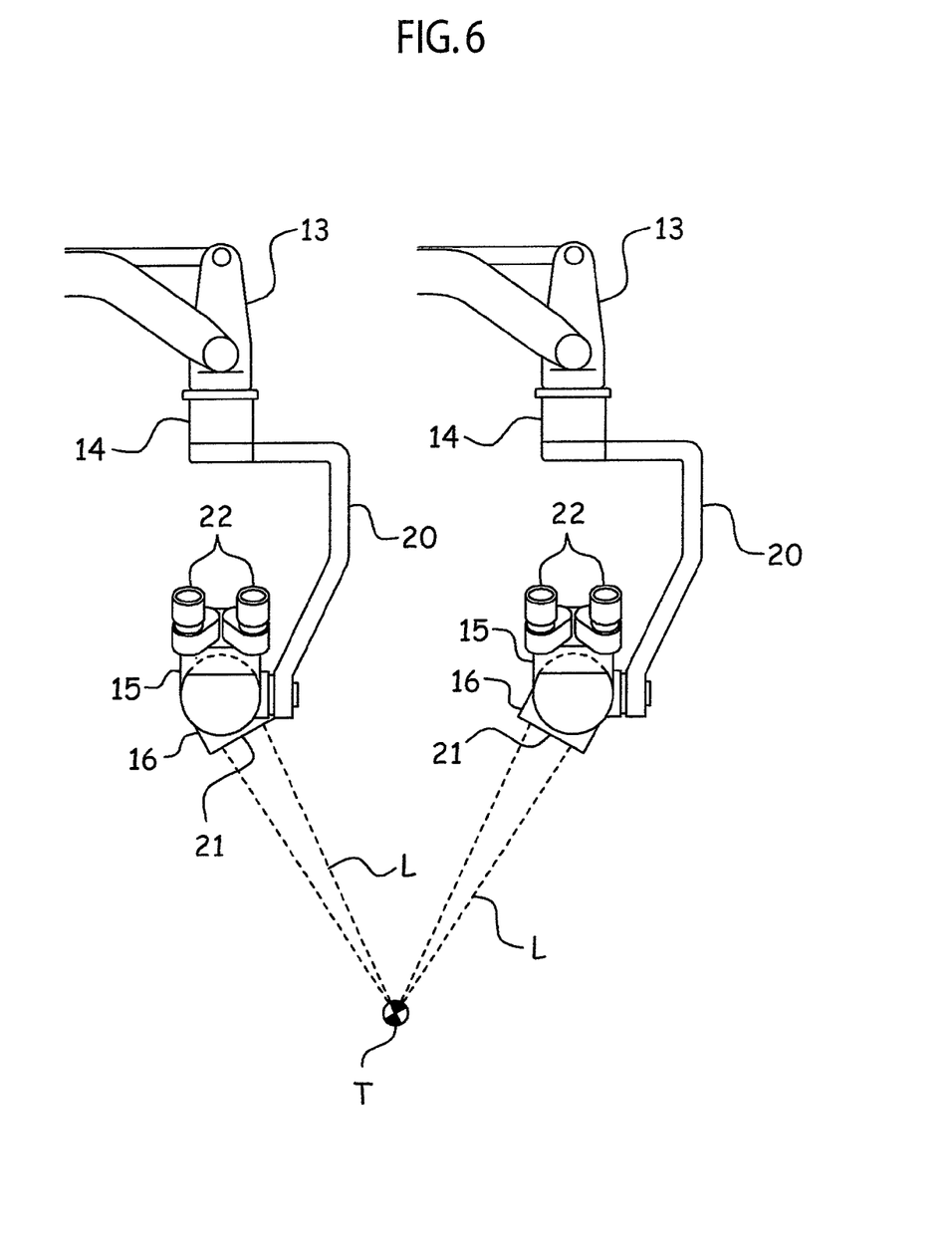
FIG. 6 is a view illustrating a turning state in a left-right direction of the surgical microscope.

When the front end part 16 is turned, the position of the surgical microscope 15 itself is changed by the stand apparatus 1 so that the observation direction of the surgical site T is optionally changed in the left-right direction as illustrated in FIG. 6. At this time, the angular position of the eyepieces 22 is unchanged, and therefore, the operator is comfortable without bending his or her neck. To hold the position of the front end part 16 in the left-right direction X, predetermined frictional force is applied between the front end part 16 and the main body of the surgical microscope 15. Instead of the frictional force, an electromagnetic clutch is adoptable to lock and free the front end part 16.

The weight of the surgical microscope 15 and the like acting on the front link 13 is entirely balanced with the counterweight 11. When the electromagnetic clutches and the like of the stand apparatus 1 are freed to move the surgical microscope 15 and the like, the surgical microscope 15 and the like stop in the air at a moved position and balance at the position even if the hands of the operator are removed from the surgical microscope 15 and the like.

The balanced state is maintained even if the surgical microscope 15 is turned in the front-rear direction Y or even if the front end part 16 is turned in the left-right direction X. Namely, the front link 13 is always maintained in the vertical position, and even if the direction of the surgical microscope 15 supported by the front link 13 through the suspension arm 20 is changed, the balanced state achieved with the counterweight 11 is unchanged to require no readjustment.

According to the embodiment mentioned above, the front end part 16 including the light flux intake 21 of the surgical microscope 15 independently turns in the left-right direction X. Even if the intake angle (observation direction) of the light flux L is changed, the angular position of the main body of the surgical microscope 15 is unchanged. This means that, even if the observation angle is changed, the operator does not need to bend his or her neck and does not need to endure a heavy burden even if the operation takes a long time.

Rotation of the front end part 16 in the left-right direction X and rotation of the surgical microscope 15 in the front-rear direction Y are irrelevant to the structure of the suspension arm 20, and therefore, the suspension arm 20 may have a simple shape. Namely, the suspension arm 20 is not required to be a parallel linkage. Due to the simple shape, the suspension arm 20 is easy to manufacture.

In the above-mentioned embodiment, the front end part 16 of the surgical microscope 15 is turned by holding the front end part 16 with the hand of the operator. Instead, the front end part 16 may have a handle (not illustrated) to be grasped by the operator when turning the front end part 16.

Second Embodiment

Figure 7:
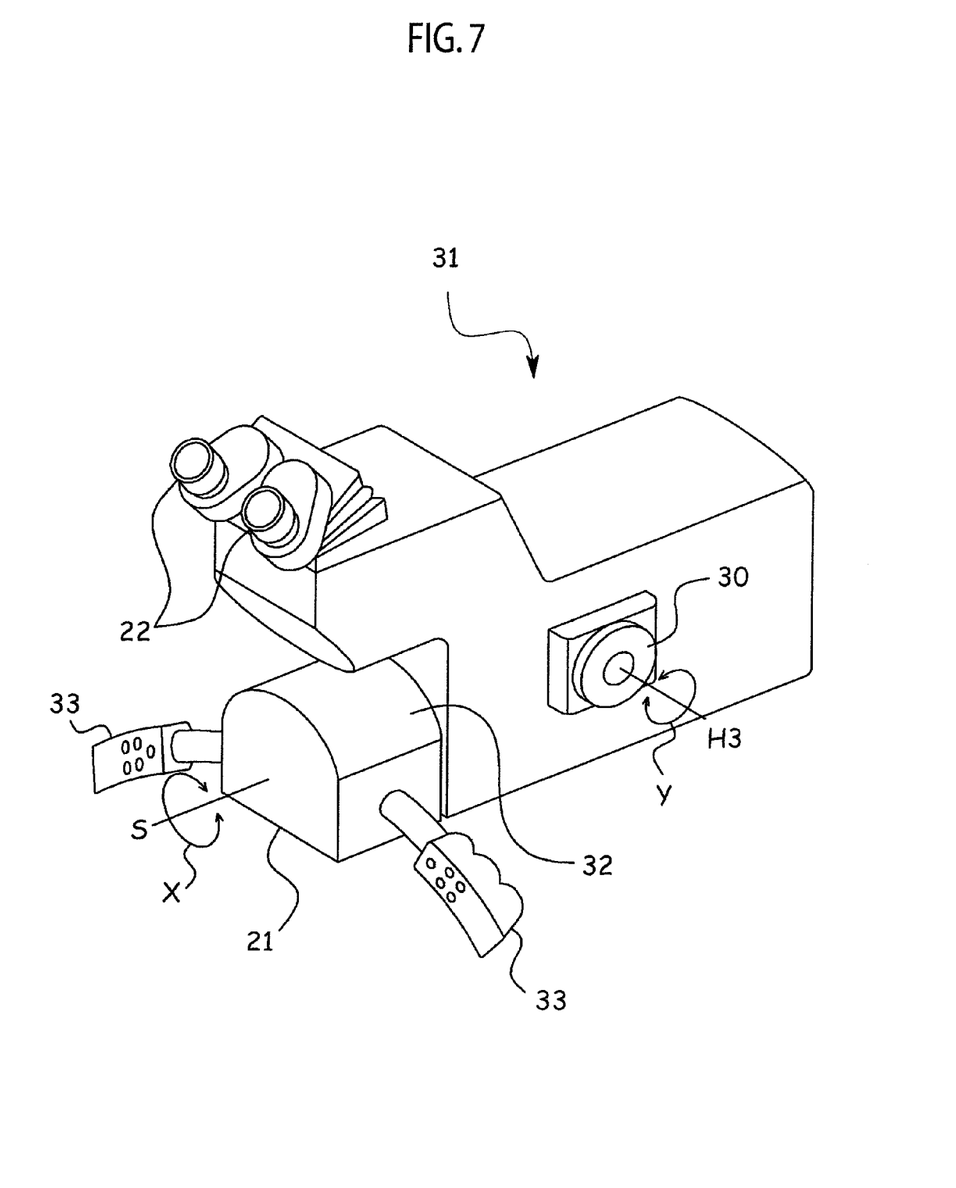
FIG. 7 is a perspective view illustrating a surgical microscope according to a second embodiment of the present invention.
Figure 8:
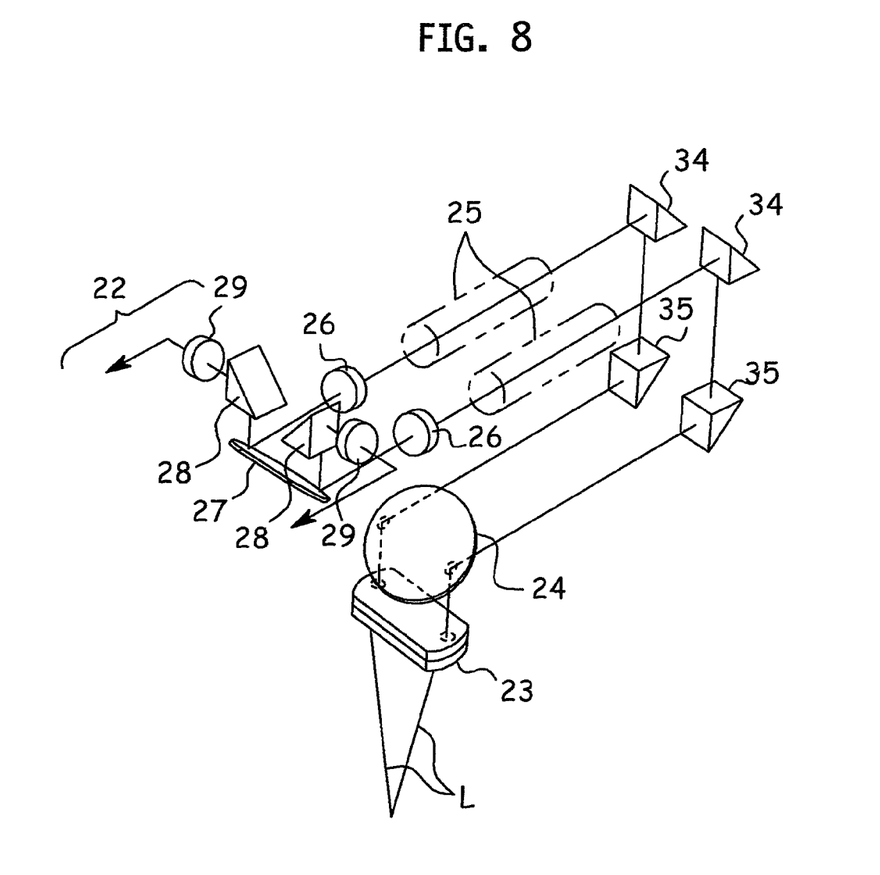
FIG. 8 is a perspective view illustrating an optical structure in the surgical microscope.

FIGS. 7 and 8 are views illustrating the second embodiment of the present invention. Structural elements of this embodiment are similar to those of the first embodiment. Accordingly, like structural elements are represented with like reference marks to omit repetition of explanation.

A surgical microscope 31 of this embodiment has a front end part 32 that includes a light flux intake 21 and is formed on an eyepieces 22 side from the position of a horizontal axis H3. On each side of the front end part 32, there is a rotation controlling handle 33.

The surgical microscope 31 incorporates two upper prisms 34 and two lower prisms 35 at ends of zoom lenses 25, to change optical paths by 180 degrees. Light flux L is guided through an object lens 23 and a first mirror 24 that are on the eyepieces 22 side, is bent by 180 degrees through the upper and lower prisms 34 and 35, and is guided to the zoom lenses 25 and eyepieces 22. The eyepieces 22 and an observing doctor are close to the front end part 32 (by the direct distance), and therefore, it is easy for the doctor to turn the front end part 32. The doctor grasps the handles 33 and can exactly turn the front end part 32. The handles 33 may be provided with buttons to adjust focusing and zooming.

Effect of Invention

According to the present invention, the front end part that is of the surgical microscope and includes the light flux intake is independently rotatable in the left-right direction. Even if an intake angle (observation direction) of light flux is changed, the angular position of the main body of the surgical microscope is unchanged. Accordingly, in response to a change in an observation angle, the operator is not required to bend his or her neck, and therefore, is free from fatigue in the neck even if the operator must conduct an operation that takes a long time.

The front end part including the light flux intake is formed on the same side as the eyepieces, and therefore, the front end part is close to the operator so that the operator can easily turn the front end part.

The front end part including the light flux intake is provided with the rotation controlling handles to easily turn the front end part.

The suspension arm is so supported as to freely rotate in a horizontal direction around a vertical axis with respect to the front end of the support arm. Accordingly, the observation direction of the surgical microscope is widely changeable in the horizontal direction.

When the support arm is turned in a longitudinal direction or when the parallel linkage as a whole is turned in a lateral direction, the front link supporting the suspension arm is always maintained in a vertical position, and therefore, the suspension arm is translated in the longitudinal and lateral directions without changing the attitude thereof. This makes it easy to move the surgical microscope to a required position.

(United States Designation)

In connection with United States designation, this international patent application claims the benefit of priority under 35 U.S.C. 119(a) to Japanese Patent Application No. 2008-210516 filed on Aug. 19, 2008, the entire contents of which are incorporated by reference herein.

The invention claimed is:

1. A surgical microscope system having a suspension arm downwardly extending from a front end of a horizontally extending support arm of a stand apparatus, a lower end of the suspension arm supporting a surgical microscope so that the surgical microscope freely turns in front-rear and left-right directions, wherein:
    the surgical microscope substantially has a cylindrical structure provided with a pair of eyepieces and an object lens, the surgical microscope including a front end part and a main body;
    the object lens being provided on the front end part, and the front end part being supported so as to turn freely and independently of the main body in the left-right direction on a principal axis passing through a center of the main body portion and a center of the front end part; and
    wherein the main body of the surgical microscope is so supported with a shaft as to freely turn in the front-rear direction relative to the lower end of the suspension arm around a horizontal axis orthogonal to the principal axis.

2. The surgical microscope system according to claim 1, wherein
    the front end part including the object lens is formed on the same side as the eyepieces with respect to the horizontal axis.

3. The surgical microscope system according to claim 1, wherein
    the front end part including the object lens intake is provided with a rotation controlling handle.

4. The surgical microscope system according to claim 1, wherein
    the suspension arm is supported at a front end of the support arm so as to freely turn in a horizontal direction around a vertical axis.

5. The surgical microscope system according to claim 1, wherein the stand apparatus is so configured that:
    in a parallel linkage having a pair of parallel longitudinal links and a pair of parallel lateral links, a lower midpoint of one of the longitudinal links is supported at a rotation axis point of a main body installed on a base;
    the upper lateral link of the parallel linkage is extended to form the support arm and a lower end of a vertical front link supported with a shaft at a front end of the support arm supports the suspension arm;
    a connection axis point of the parallel linkage that serves as a start point of the support arm supports with a shaft a crank member having a horizontal axis point positioned on a horizontal line on which the connection axis point is present and a vertical axis point positioned on a vertical line on which the connection axis point is present;

the horizontal axis point of the crank member is connected to a part of the main body with a longitudinal sub-link that is in parallel with a virtual straight line between the connection axis point and rotation axis point of the longitudinal link and has the same length as the straight line and the vertical axis point of the crank member is connected to a part of the front link with a lateral sub-link that is in parallel with a virtual straight line between the connection axis point and front end of the support arm and has the same length as the straight line; and a counterweight is arranged at a lower part of the parallel linkage, to cancel weight acting in a rotation direction of the parallel linkage around the rotation axis point and weight acting in a rotation direction of the support arm around the connection axis point.

6. The surgical microscope system according to claim 1, wherein the suspension arm is supported at a front end of the support arm so as to freely turn in a horizontal direction on a vertical axis, and wherein a point at which the horizontal axis intersects the principal axis lies on the vertical axis.

* * * * *